United States Patent [19]

Larsen et al.

[11] Patent Number: 5,130,731
[45] Date of Patent: Jul. 14, 1992

[54] FILM HOLDER

[75] Inventors: Robert M. Larsen, Quincy; Leonard Polizzotto, Stow, both of Mass.

[73] Assignee: Polaroid Corporation, Cambridge, Mass.

[21] Appl. No.: 655,333

[22] Filed: Feb. 14, 1991

[51] Int. Cl.⁵ .............................................. G03B 17/26
[52] U.S. Cl. .................................. 354/276; 354/283; 354/277
[58] Field of Search .............. 354/86, 88, 276, 277, 354/283; 206/455; 250/475.2, 484.1, 485.1; 378/172–174

[56] References Cited

U.S. PATENT DOCUMENTS

| | | | |
|---|---|---|---|
| 828,669 | 8/1906 | Klenck | 354/277 X |
| 2,450,841 | 10/1943 | Moore | 354/276 |
| 2,629,303 | 2/1953 | Grant, Jr. | 354/277 |
| 2,709,223 | 5/1955 | Bachelder et al. | 354/276 |
| 2,834,271 | 5/1958 | Booth | 354/86 |
| 3,747,496 | 7/1973 | Bahnsen | 354/276 |
| 4,186,308 | 1/1980 | Erikson | 354/276 X |
| 4,804,989 | 2/1989 | Kumanomido | 354/283 |
| 4,833,493 | 5/1989 | Lamar | 354/285 X |
| 4,903,063 | 2/1990 | Hara | 354/277 |
| 5,008,694 | 4/1991 | Tajima et al. | 354/277 |

Primary Examiner—L. T. Hix
Assistant Examiner—D. Rutledge
Attorney, Agent, or Firm—John J. Kelleher

[57] ABSTRACT

A film holder provides a lighttight environment where a film unit may be inserted while enclosed within a lighttight envelope. After insertion the envelope may be removed from the film unit to allow the exposure of the film unit by a source of electromagnetic radiation mounted on one wall of the holder. The source of electromagnetic radiation is mounted on a block to reciprocate back and forth toward the film surface to allow the source of electromagnetic radiation to press against the film unit when the envelope is retracted from the holder and the block may be withdrawn from contact with the film unit to allow the reinsertion of the envelope to cover the exposed film unit.

21 Claims, 3 Drawing Sheets

FILM HOLDER

BACKGROUND OF THE INVENTION

1. Field of the Invention

This invention relates to a manually portable film holder which provides a lighttight environment for photographic film. A film unit inside an opaque envelope, which may also include a conventional darkslide, may be inserted through an opening in one sidewall of the film holder, and after the unit is enclosed within the lighttight environment of the holder, the envelope (and/or the darkslide) is retracted, thereby uncovering the film unit for exposure to light or to some other type of electromagnetic radiation. A preferred source of electromagnetic radiation comprises an electrophoresis gel mounted on a block within the lighttight film holder. The electrophoresis gel is reciprocable into and out of surface contact with the film unit to allow the exposure to electromagnetic radiation from an isotope or chemiluminescence label. The gel is pressed against the photosensitive material of the film unit for a predetermined period of time, and after that time period has elapsed the gel is retracted from the film unit, the envelope (or the dark slide) is then reinserted to cover the exposed film, and the envelope and film unit are extracted from the holder for subsequent instant or non-instant type developing.

2. Description of the Prior Art

Film holders for instant or self-developing, peel-apart, sheet film are numerous. The holders may be either a separate opaque film holder or a camera back which allows for loading of film into the lighttight holder for subsequent exposure by some specified means while within the holder.

A particular problem involves the exposure of a film unit by an electrophoresis gel containing a DNA or a protein material while within a lighttight environment for some specified period of time which may be for minutes or days, depending upon various physical properties. The exposed film unit is developed by conventional methods and the photographic image of the DNA material is then available for subsequent analysis of the associated DNA sequencing defining such material.

Custom made electrophoresis gel, in sheet form, is presently available from a number of suppliers. A customer who might be interested in the DNA sequencing of some animal tissue, fluid, etc. may send the material in question to the supplier for inclusion in an electrophoresis gel. A part of the process of preparing the gel is to place the submitted material that includes the particular isotope or chemiluminescence label on a gel which is appropriate for the particular material. An electrical current is then passed through the gel to properly distribute or orient the DNA for subsequent image transferring purposes. The gel is then formed into a solid sheet-like material which is then returned to the customer. The process for formation of the gel is well known and is not a part of this invention.

At the present time DNA images are formed on film by placing the electrophoresis gel against a sheet of photosensitive material and maintaining them in firm contact for the specified period. The placement of the electrophoresis gel against the photosensitive material and the image transferring process must take place in a darkroom to prevent inadvertent exposure of the film unit. This is obviously a difficult and time consuming chore. There is a need for an apparatus which provides a manually portable film holder-darkroom which allows the photosensitive film unit to be handled in ambient light. A manually portable film holder which will allow the daylight insertion of a film unit into the holder combined with a means to press the electrophoresis gel against the photosensitive material while within the film holder is desirable.

U.S. Pat. No. 3,747,496 discloses a film unit in an opaque envelope, a means for opening the envelope while it is inside a camera, taking a photograph to expose the film unit, reinserting the envelope into the camera around the exposed film unit, and removing the envelope to allow the film unit to develop. This broad technique has been well known for many years. U.S. Pat. Nos. 4,804,989; 4,833,493; and 4,903,063 all disclose alternative structures involving means for exposing a film unit in a particular film holder environment. Various structures are shown in those patent disclosures and drawings for maintaining a lighttight environment during the whole procedure.

U.S. Pat. No. 2,450,841 discloses a film holder for use in the photographic industry and a peripheral structure around the edge of the two mating parts of the film holder includes a tongue-in-groove arrangement to prevent the incursion of light from the mating sides of the two parts of the film holder.

U.S. Pat. No. 2,834,271 discloses the use of pile fabric around an exit from a film holder where the film unit passes through an opening lined with pile fabric. The pile fabric allows the film unit to slip through the opening while the pile fabric is displaced and without allowing light to penetrate.

In an electrophoresis gel application involving pressing the gel against photosensitive material, the means for achieving the pressure required is a consideration and U.S. Pat. No. 2,709,223 shows a technique for applying pressure against a photosensitive sheet.

SUMMARY OF THE INVENTION

A film holder according to the preferred embodiment of this invention includes an opaque bottom having upstanding sidewalls about its periphery. The upstanding sidewalls terminate in a transversely extending shelf to thereby frame a film exposure opening.

A slot opening through one of the sidewalls allows the insertion and removal of a film unit which is enclosed in an opaque envelope to prevent exposure of the film unit while it is outside the film holder. A darkslide may also be included within the envelope. The slot opening includes a border of felt or fabric not greatly different from that illustrated in U.S. Pat. No. 2,834,271. The film unit itself may be a single sheet film or a film cassette holding more than one film unit. Each film unit inserted into the holder may include a pod of developer liquid which will be disposed adjacent and parallel with the slot opening through the sidewall.

Two rollers are mounted parallel with and outwardly of the felt lined slot for purposes of rupturing the pod of developer liquid on the film unit when it is extracted from the holder after exposure. The rollers rupture the pod and spread the developer liquid on the exposed film unit to effect development of a visible image on the photosensitive material within about 60 seconds of the time the film unit is withdrawn from the holder. The developing process takes places while the photosensitive material is enclosed within the opaque envelope. In a similar arrangement, the rollers form a part of a separate conventional lighttight processor, and the rollers of the processor rupture a pod of developer liquid and spread its contents between an exposed negative and a positive sheet as they exit from a cassette located within the separate processor. A representative example of a cassette of this type is shown in commonly assigned U.S. Pat. No. 4,186,308 to Erikson.

The film unit is exposed to electromagnetic radiation while within the holder after the envelope or darkslide has been stripped from the film unit and held in place for subsequent use outside the film holder. The envelope or darkslide is reinserted into the holder to cover the exposed film unit after exposure has taken place and then the envelope or darkslide and exposed film unit in combination are withdrawn from the holder through the slot in the sidewall and through the pair of rollers either adjacent thereto or those forming a part of the separate processor, which rupture the pod of developer liquid. In an arrangement where a separate processor is employed, a conventional film unit enclosing opaque envelope also contains a conventional light blocking darkslide (not shown). Both the envelope and the darkslide are removed from film unit exposure while the film unit is within the film holder. However, the envelope is then discarded and only the darkslide is reinserted to cover the exposed film unit after exposure has occurred.

The film holder operates in combination with a lid of the same general rectangular configuration as the lower section of the holder. It is mechanically locked in place on the lower section. The lid is configured to block the film exposure opening defined by the transversely extending shelf at the upper extension of the sidewalls. Thereby the combination provides a manually portable darkroom for a film unit which allows the film unit within an opaque envelope to be inserted into the holder while in ambient light and without any exposure of the photosensitive material on the film unit when it is inserted into the holder.

A mounting block is reciprocally mounted in the lid. The inner face of the block is generally planar and designed to mount a sheet of electrophoresis gel on the flat block surface to face toward the film unit after the envelope and/or darkslide is stripped from it.

Mechanical means are provided to hold the block and sheet of electrophoresis gel out of pressure contact with the surface of the envelope and film unit until the envelope and/or darkslide has been extracted from the holder. Thereafter mechanical force, preferably manual force, is applied to the block from outside the enclosure to overcome the mechanical force holding the block. The electrophoresis gel is pressed tightly against the surface of the film unit and the isotope contained within the gel will serve to expose the photosensitive material in some specified time, from minutes to days.

A mechanically biasing means is connected to the block and to the lid to bias the block downward into pressure contact with the film unit after the mechanical force holding the block in a retracted position has been overcome. Preferably the biasing means is an opaque elastomeric material bridging the space between the block and the lid to serve both as a biasing means and as an opaque curtain to block the incursion of light into the film holder.

Objects of the invention not clear from the above summary will be more fully understood from the following detailed description of the preferred embodiment and a review of the accompanying drawings.

DETAILED DESCRIPTION OF THE PREFERRED EMBODIMENT

Figure 1:
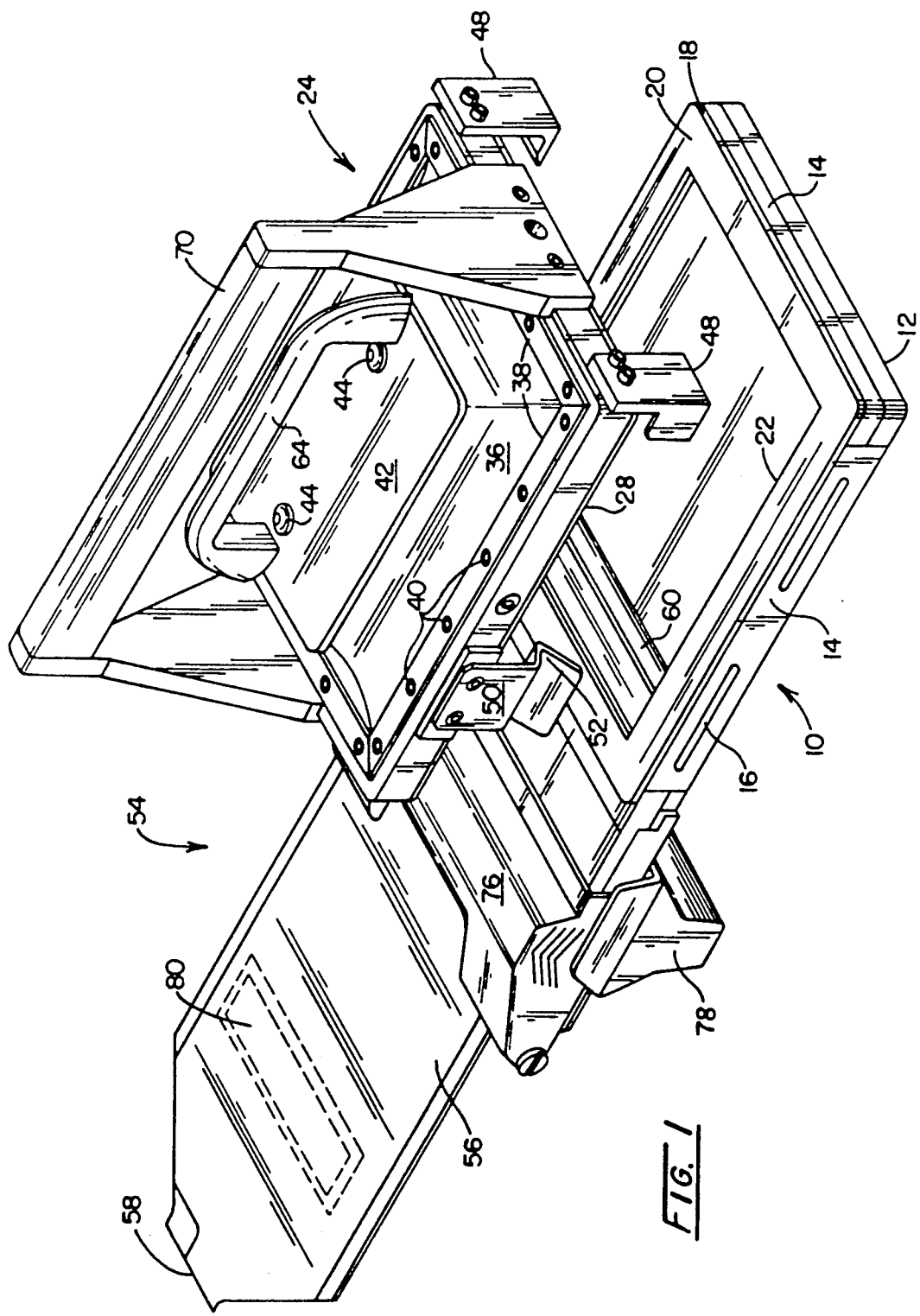
FIG. 1 is an exploded perspective view of the film holder according to this invention.

Looking to the drawings, a film holder according to this invention provides a manually portable darkroom which allows a film unit to be inserted into the film holder where it may be exposed to some kind of light or other type of electromagnetic radiation under the control of the user, without the film unit being exposed to such radiation while the film unit is being inserted into the holder in ambient light conditions.

The holder includes a lower section 10 which has an opaque bottom 12 and upstanding sidewalls 14. Note that the sidewalls includes a groove 16 in two opposite sides at their exterior. The function of the grooves will be explained subsequently.

The sidewalls 14 terminate at their upper end in a transversely extending shelf 18. In the illustrated preferred embodiment the shelf 18 is planer across its full surface and parallel with the bottom. Shelf 18 is covered with a felt pad 20.

Together the lower section bottom 12 and sidewalls 14 form a cavity, and the shelf 18 frames an open top 22 of generally rectangular configuration. It will be understood from the subsequent discussion that the open top 22 could be of any geometric configuration as desired and it need not be rectangular.

The light admitting open top 22 is closed to external light to form a lighttight compartment by a lid 24. Note that the lid includes about its periphery a transversely extending surface 26 which is covered with a felt pad 28. Pad 28 mates with the felt pad 20 attached to the shelf 18 and together they provide a lighttight engagement about the periphery of the opening 22.

A mounting block 30 is reciprocally mounted in the lid and includes a flat surface 32 suitable for mounting a sheet of electrophoresis gel 34. Preferably the gel sheet is mounted on the flat surface 32 by a double-sided adhesive tape (not shown). In this case the flat mounting surface 32 is shown as a separate element from block 30 but that is optional.

The block 30 is biased toward the interior of the film holder by an opaque black elastomeric sheet 36 which is connected to the lid proper by a plurality of plates 38 and screws 40 which clamp the edges of the elastomeric sheet against the upper surface of the lid 24. In the preferred embodiment, best illustrated in FIG. 3, the elastomeric sheet extends completely across the top of the block 30 and is secured to the block by a flat plate 42 and screws 44 in combination.

Figure 3:
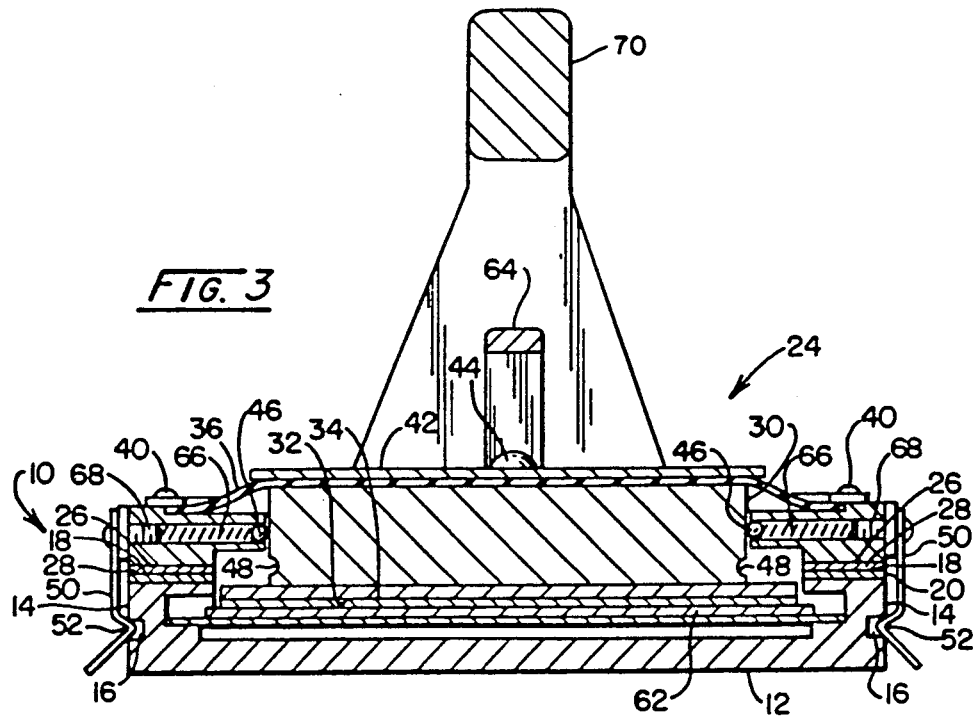
FIG. 3 is a sectional view of the film holder of FIG. 2 taken along line 3—3 in FIG. 2.

The block 30 is reciprocable between a lowered position as illustrated in FIG. 3 and a retracted position where the block 30 and sheet of gel 34 are retracted or moved upward. When the block is pulled upward a set of ball bearings 46 housed in the lid slip into dimples 48 in the sides of the block 30. The ball bearings 46 are spring-biased toward the block and when engaging the dimples 48 will hold the block 30 in the retracted position for reasons which will be explained subsequently. Note that the preferred embodiment includes four ball bearings and four dimples, one cooperating pair consisting of a dimple and a ball bearing near each corner of the block 30.

Two L-shaped brackets 48 are bolted to two corners of the lid and are designed to slip under and along the side of the lower section of the film holder 10, and with the L-shaped brackets 48 in locked position a pair of leaf springs 50 having offset portions 52 cooperate to lock into grooves 16 in the exterior sidewalls 14, best seen in FIG. 3.

Figure 4:
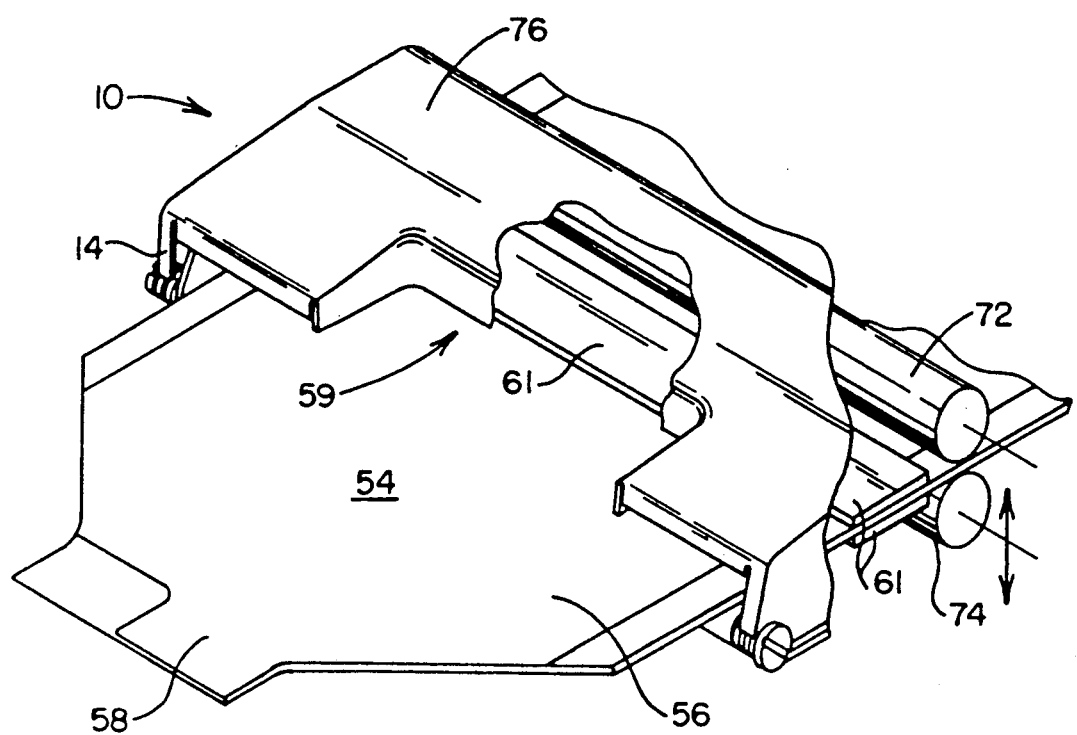
FIG. 4 is a fragmentary schematic view of the slot in the film holder to receive the inserted film unit.

In operation, a film unit indicated generally at 54 includes a thin felt opaque envelope 56, having a grasping tab 58 on one end, is inserted into the lower section 10 of the holder through a slot opening 59 in one sidewall 14. The slot opening is lined with a felt material 61 to closely encompass the surface of the envelope 56 as it is inserted through the slot and as it is later removed. The felt border around the slot opening serves the purpose of maintaining lighttight conditions within the holder while the envelope is projecting through the slot, see FIG. 4.

Note that the innermost end of the film unit 54 includes a plastic or metallic end cap element 60 at its forward edge which serves two purposes. The first purpose is to provide structural stability to prevent distortion of the film unit, and the second purpose is to provide a locking engagement by a finger or hook (not shown) at the right-hand side of the lower section 10 which will engage the metal element 60 for reasons which will be explained subsequently.

A sheet of electrophoresis gel 34 is mounted on the flat plate surface 32 of the block 30 and the lid 24 is moved into position by fitting each of the L-shaped brackets 48 against the corners of lower section 10 with one leg beneath the bottom surface 12 and along its sidewalls while the lid is tilted upward. Then the lid is pivoted downward into place and the sidewalls 14 cam the leaf springs 50 outwardly until the offset 52 reaches the grooves 16 in the sidewalls 14 of the lower section. The inward spring bias of the leaf springs 50 snap the offsets 52 into the grooves 16 to lock the lid in position and form the manually portable darkroom or lighttight compartment for use by the operator.

When the lid 24 is rotated into locked position, the film unit 54 is completely inserted while the mounting block 30 is in its retracted or in its uppermost position with the ball bearings 46 resting within the dimples 48. After the lid 24 is locked in its lighttight position, the envelope 56 is retracted from the holder through the slot opening 59 by pulling the tab 58. However, the light-sensitive portion 62 of the film unit is retained within the lighttight holder by the end cap latch or hook which grasps the metal end cap element 60 of the film unit 54 and holds the light-sensitive layer within the film holder when the envelope is withdrawn. If the envelope also encloses a darkslide, as in the case where a separate processor is employed, the darkslide is withdrawn also.

After the envelope 56 and/or darkslide has been pulled out of the area defined by the frame 22, downward manual pressure is applied to the handle 64. The handle 64 is attached directly to the mounting block 30 and downward pressure on handle 64 depresses the mounting block 30 and its attached layer of gel 34. Obviously the downward force must be sufficient to overcome the holding force of the spring-biased ball bearings 46 in the dimples 48. Accordingly the springs 66 are adjusted to a minimum holding force by screws 68. When the ball bearings 46 are displaced, the downward bias of the elastomeric sheet 36 will press the electrophoresis gel 34 tightly against the photosensitive layer 62 of the film unit and the radioactive isotope within the gel will expose the photosensitive portions of the film unit. The firm physical contact between the gel layer and the photosensitive layer will be maintained for a prescribed period.

After suitable exposure, the block 30 is retracted manually by the users hand. The palm of the hand rests on upper handle 70 and the fingers slide under handle 64. As the fingers curl the block rises until the ball bearings 46 snap into dimples 48. The ball bearings again engage the dimples 48 and hold the block out of pressing engagement with the film unit 62. Then the envelope 56 (or darkslide)is reinserted to cover the exposed film unit 62. The locking finger or hook is disengaged from its holding position on element 60 and together the exposed photosensitive element 62 is withdrawn from the holder enclosed within the opaque envelope 56 (or covered by the darkslide) for conventional instant or non-instant type development outside the film holder.

Figure 2:
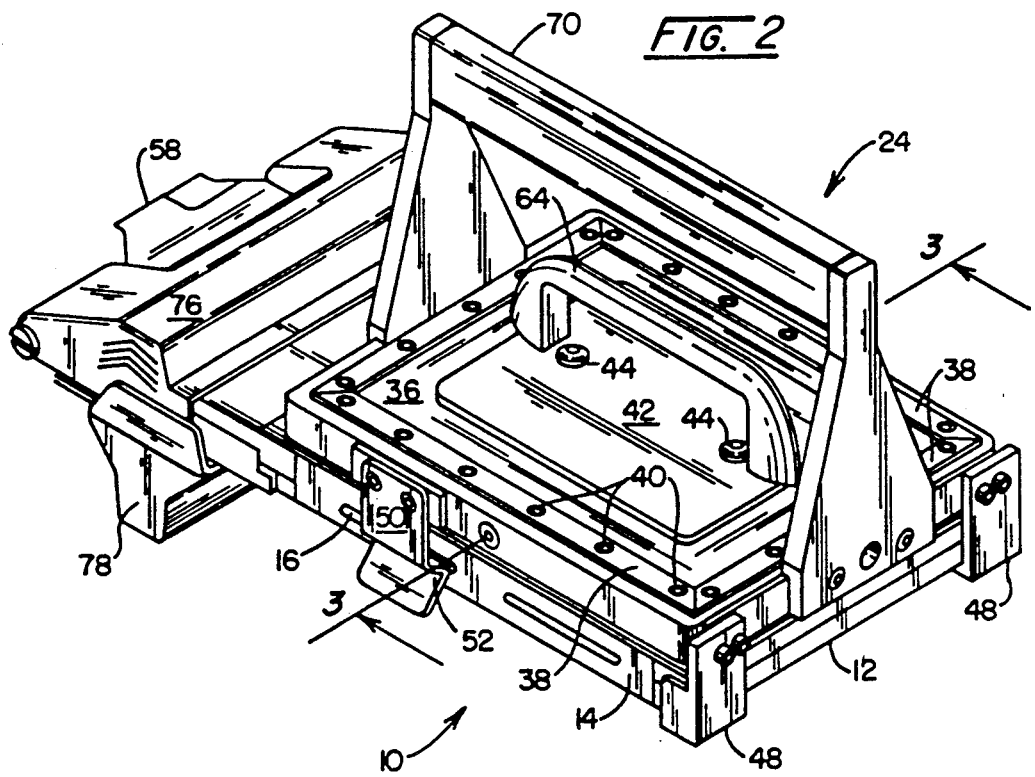
FIG. 2 is a perspective view of the film holder of this invention with the lid clamped into place on the holder.

In the preferred embodiment a pair of conventional spread rollers 72, 74 are mounted parallel to and adjacent the slot through which the film unit 54 is inserted and removed. The rollers are housed in enlargements 76, 78 at the left-hand side of the film holder as shown in FIG. 2.

The preferred film unit includes a rupturable pod of developer liquid 80 at the end of the film unit nearest the tab 58. The pair of rollers 72, 74 are adjustable to an inoperative position during the insertion of the film unit 54 and at the time of the initial retraction of the opaque envelope 56. Then when the exposed film unit is to be removed for developing, the pair of rollers may be adjusted to rupture the pod of developer liquid and spread it along the surface of the exposed light-sensitive layer as the envelope and photosensitive layer are simultaneously removed. The conventional time for development under these circumstances is about one minute at which time the envelope 56 may be stripped off the light-sensitive layer 62 and the developed layer will be available for use as needed.

Since certain changes may be made in the above described apparatus without department from the scope of the invention herein involved, it is intended that all matter contained in the above description or shown in the accompanying drawings shall be interpreted as illustrative and not in a limiting sense.

What is claimed:

1. A film holder comprising,
    a lower section having an opaque bottom and upstanding sidewalls, said bottom and sidewalls combining to form an open topped cavity, said upstanding sidewalls terminating at their upper edge in a transversely extending shelf;
    an opening through one of said sidewalls, said opening being configured to seal the cavity from light while allowing the passage of a thin, flat, opaque envelope containing a film unit and/or a darkslide therethrough;
    means for (1) releasably holding the film unit within said lower section after the film unit, an envelope and/or a darkslide are inserted through said opening and after the envelope and/or darkslide is withdrawn and (2) releasing the film unit for withdrawal from said lower section after the film unit has been exposed to electromagnetic radiation and the envelope or darkslide has been reinserted to respectively enclose or cover the exposed film unit;

an opaque lid of a shape and size to cover the open top of the cavity formed by the lower section, said lid including a transversely extending surface configured to mate with said shelf at the upper edge of said sidewalls, said surface and shelf including means to provide a lighttight seal about the periphery of said cavity in said lower section;

means for releasably locking said lid to said lower section to form a lighttight cavity; and a retractable pressure block mounted on said lid, said block serving as a mounting for a source of film exposing electromagnetic radiation, said mounting for the source of electromagnetic radiation including a planar surface facing toward said cavity, means for holding said block and the source out of pressure contact with the envelope and/or darkslide when the envelope and/or darkslide is in said cavity, and means for biasing said block and the source toward the film unit after the envelope and/or darkslide is withdrawn from said cavity.

2. A film holder comprising, a lower section having an opaque bottom and upstanding sidewalls, said bottom and sidewalls combining to form an open topped cavity, said upstanding sidewalls terminating at their upper edge in a transversely extending shelf;

an opening through one of said sidewalls, said opening being configured to seal the cavity from light while allowing the ingress and egress of a thin, flat, opaque envelope containing a film unit, the film unit including a rupturable pod of film developer liquid at one end thereof;

retractable roller means on said lower section adjacent said opening, means for moving said roller means from an inoperative position where the pod may pass through said opening without being ruptured by said roller means to an operative position where the roller means ruptures said pod and spreads the developer liquid over the film unit when the envelope and the film unit are withdrawn from the lower section through said opening;

means for (1) releasably holding the film unit within said lower section after the film unit and envelope are inserted through said opening and after the envelope is withdrawn and (2) releasing the film unit for withdrawal from said lower section after the film unit has been exposed to electromagnetic radiation and the envelope been reinserted to enclose the exposed film unit;

an opaque lid of a shape and size to cover the open top of the cavity formed by the lower section, said lid including a transversely extending surface configured to mate with said shelf at the upper edge of said sidewalls, said surface and shelf including means to provide a lighttight seal about the periphery of said cavity in said lower section;

means for releasably locking said lid to said lower section to form a lighttight cavity; and a retractable pressure block mounted on said lid, said block serving as a mounting for a source of film exposing electromagnetic radiation, said mounting for the source of electromagnetic radiation including a planar surface facing toward said cavity, means for holding said block and the source out of pressure contact with the envelope when the envelope is in said cavity, and means for biasing said block and the source toward the film unit after the envelope is withdrawn from said cavity.

3. The film holder of claim 2 wherein said means for biasing said block toward the film unit comprises an elastomeric sheet in tension clamped to said lid and extending in light blocking relationship between said block and said lid.

4. The film holder of claim 3 wherein said means for holding said block and electromagnetic radiation source out of pressure contact with the envelope comprises a plurality of spring biased balls fitting into dimples, said balls and dimples being in either of said block or said lid and there being at least one dimple for each ball, the direction of said spring bias of said balls being transverse to the direction of the bias of said block toward the film unit.

5. The film holder of claim 4 wherein said means for locking said lid to said lower section includes a leaf spring attached to either said lid or said lower section, said leaf spring including an offset, a groove in the other of said lid or said lower section to receive said offset of said leaf spring in locking engagement by a spring biased deflection of said leaf spring.

6. The film holder of claim 5 including at least one L-shaped bracket having one leg of said L-shaped bracket secured to said lid at its edge, the other leg of said L-shaped bracket being oriented to slide under said bottom of said lower section and at a location spaced from said opening through said lower section sidewall.

7. The film holder of claim 6 including at least two leaf springs on said lid, said leaf springs being on opposite sides of said lid and depending downwardly to straddle said lower section intermediate said L-shaped bracket and said sidewall opening.

8. The film holder of claim 7 wherein said lid, open topped cavity, pressure block and lower section are all generally rectangular and there are two generally L-shaped brackets at two corners of said lid to fit around both surfaces of two adjacent corners of said lower section.

9. The film holder of claim 2 including at least one L-shaped bracket having one leg of said L-shaped bracket secured to said lid at its edge, the other leg of said L-shaped bracket being oriented to slide under said bottom of said lower section and at a location spaced from said opening through said lower section sidewall.

10. The film holder of claim 9 including at least two leaf springs on said lid, said leaf springs being on opposite sides of said lid and depending downwardly to straddle said lower section intermediate said L-shaped bracket and said sidewall opening.

11. The film holder of claim 10 wherein said lid, open topped cavity, pressure block and lower section are all generally rectangular and there are two generally L-shaped brackets at two corners of said lid to fit around both surfaces of two adjacent corners of said lower section.

12. The film holder of claim 11 wherein said means for holding said block and electromagnetic radiation source out of pressure contact with said envelope comprises a plurality of spring biased balls fitting into dimples, said balls and dimples being in either of said block or said lid and there being at least one dimple for each ball, the direction of said spring bias of said balls being transverse to the direction of the bias of said block toward the film unit.

13. The film holder of claim 2 wherein said means for holding said block and electromagnetic radiation source out of pressure contact with the envelope comprises a plurality of spring biased balls fitting into dimples, said balls and dimples being in either of said block or said lid and there being at least one dimple for each ball, the direction of said spring bias of said balls being transverse to the direction of the bias of said block toward the film unit.

14. The film holder of claim 13 including at least one L-shaped bracket having one leg of said L-shaped bracket secured to said lid at its edge, the other leg of said L-shaped bracket being oriented to slide under said bottom of said lower section and at a location spaced from said opening through said lower section sidewall.

15. The film holder of claim 14 including at least two leaf springs on said lid, said leaf springs being on opposite sides of said lid and depending downwardly to straddle said lower section intermediate said L-shaped bracket and said sidewall opening.

16. The film holder of claim 3 wherein said means for locking said lid to said lower section includes a leaf spring attached to either said lid or said lower section, said leaf spring including an offset, a groove in the other of said lid or said lower section to receive said offset of said leaf spring in locking engagement by a spring biased deflection of said leaf spring.

17. The film holder of claim 16 including at least one L-shaped bracket having one leg of said L-shaped bracket secured to said lid at its edge, the other leg of said L-shaped bracket being oriented to slide under said bottom of said lower section and at a location spaced from said opening through said lower section sidewall.

18. The film holder of claim 17 including at least two leaf springs on said lid, said leaf springs being on opposite sides of said lid and depending downwardly to straddle said lower section intermediate said L-shaped bracket and said sidewall opening.

19. The film holder of claim 18 wherein said lid, open topped cavity, pressure block and lower section are all generally rectangular and there are two generally L-shaped brackets at two corners of said lid to fit around both surfaces of two adjacent corners of said lower section.

20. The film holder of claim 2 wherein said means for locking said lid to the lower section includes a leaf spring attached to either said lid or said lower section, said leaf spring including an offset, a groove in either said lid or said lower section to receive said offset of said leaf spring in locking engagement by a spring biased deflection of said leaf spring.

21. The film holder of claim 20 including at least one L-shaped bracket having one leg of said L-shaped bracket secured to said lid at its edge, the other leg of said L-shaped bracket being oriented to slide under said bottom of said lower section and at a location spaced from said opening through said lower section sidewall.

* * * * *